United States Patent [19]

Turner

[11] Patent Number: 5,296,216
[45] Date of Patent: Mar. 22, 1994

[54] PREVENTION AND TREATMENT OF ORAL LESIONS

[76] Inventor: Robert E. Turner, 421 Marble Dr., Coraopolis, Pa. 15108

[21] Appl. No.: 766,365

[22] Filed: Sep. 25, 1991

Related U.S. Application Data

[63] Continuation of Ser. No. 423,500, Oct. 12, 1989, which is a continuation of Ser. No. 26,738, Mar. 17, 1987, abandoned.

[51] Int. Cl.$^5$ .......................... A61K 7/16; A61K 7/20; A61K 33/40; A61K 33/10
[52] U.S. Cl. ..................................... 424/53; 424/616; 424/717
[58] Field of Search ........................... 424/53, 616, 717

[56] References Cited

U.S. PATENT DOCUMENTS

| | | | |
|---|---|---|---|
| 3,729,553 | 4/1973 | Gold et al. | 424/44 |
| 4,024,237 | 5/1977 | Eichel et al. | 424/53 |
| 4,132,770 | 1/1979 | Barth | 424/49 |
| 4,250,168 | 2/1981 | Crawford | 424/717 |
| 4,606,912 | 8/1986 | Rudy et al. | 424/717 |
| 4,776,500 | 10/1988 | Ford | 424/53 |
| 4,868,161 | 9/1989 | Roberts | 424/616 |
| 4,971,782 | 11/1990 | Rudy et al. | 424/616 |
| 5,008,106 | 4/1991 | Merianos et al. | 424/53 |
| 5,039,515 | 8/1991 | Korf | 424/53 |
| 5,104,644 | 4/1992 | Douglas | 424/53 |

FOREIGN PATENT DOCUMENTS

| | | | |
|---|---|---|---|
| 944506 | 4/1949 | France | 424/53 |

Primary Examiner—Shep K. Rose
Attorney, Agent, or Firm—Arnold, White & Durkee

[57] ABSTRACT

The present invention involves a preparation adapted for prophylaxis and treatment of oral lesions. The preparation is suitable for use as an oral lavage, and comprises water, hydrogen peroxide in a premixed aqueous form in the preparation mixture, with between about 0.1% and about 0.4% sodium bicarbonate. To produce such a preparation adapted for the prophylaxis and treatment of oral lesions most preferably involves dissolving hydrogen peroxide and sodium bicarbonate in an aqueous solution to produce a premixed preparation having between about 0.1% and about 0.8% hydrogen peroxide and between about 0.1% and about 0.4% sodium bicarbonate. In more preferable embodiments of the present invention, the oral lavage (formulation) includes hydrogen peroxide at a concentration of about 0.4% and sodium bicarbonate at a concentration of about 0.2%. Additionally, a method for prophylaxis and treatment of oral lesions incident the use of chemotherapeutic agents is included in the present invention. This method involves the step of initially providing a premixed preparation comprising water, between about 0.1% and about 0.8% hydrogen peroxide and between about 0.1% and about 0.4% sodium bicarbonate. Oral rinsing with said preparation, particularly multiple daily oral rinsing, is shown to enhance healing of oral lesions and impedes or prevents the development of oral lesions.

21 Claims, No Drawings

PREVENTION AND TREATMENT OF ORAL LESIONS

The present application is a continuation of U.S. Ser. No. 07/423,500 filed Oct. 12, 1989 which is a continuation of U.S. Ser. No. 07/026,738, filed Mar. 17, 1987, from which priority is claimed. U.S. Ser. No. 07/026,738, filed Mar. 17, 1987, is now abandoned. U.S. Ser. No. 07/423,500 was filed as a file wrapper continuation of U.S. Ser. No. 07,026,738 on Oct. 12, 1989. U.S. Ser. No. 07/423,500 is pending. A continuous chain of copendency has been maintained between the presently filed application and U.S. Ser. No. 07/026,738, thereby maintaining a claim to priority to the Mar. 17, 1987 filing date of the grandparent application, U.S. Ser. No. 07,026,738.

BACKGROUND OF THE INVENTION

The present invention relates to a composition and method of prophylaxis and treatment for oral mucosal lesions. Oral lesions of various forms may develop in many circumstances and conditions. These forms of oral lesions include, for example, ulcerations, infections, stomatitis and vesiculo-bullous lesions. Among the most acute of these oral lesions are those typically occurring as an incident to cancer chemotherapy. These chemotherapy-related lesions may be so painful and severe as to force cessation of the chemotherapy, as well as eating and drinking, which may interfere with medical treatment. The lack of a consistent, effective and convenient method of prophylaxis and treatment for such oral lesions has too long been a therapeutic handicap.

Certain antineoplastic drugs have well documented direct and indirect stomatotoxicity. The direct toxicity is characterized by the interruption of the migrating, maturing squamous cells from the basal cell layer to the oral mucosal surface. As this normal progression is attenuated and desquamation of surface cells continues, it may be clinically manifested as oral mucosal ulcerations. Acute and severe pain may be associated with this ulcerative process at its developmental peak. Patients have discontinued their chemotherapy due to this complication. Such cessation means that the full chemotherapy protocol cannot be delivered and thus, the patient may not be provided the best therapeutic effect. Control or cure of the cancer may be lost. The patient and family are then placed in an emotional struggle between gaining relief from the oral pain and simultaneously realizing that in doing so the cancer may continue to progress.

The indirect stomatotoxic effects are related to alteration of the hematologic status through myelosupression and the patient's subsequent decreased ability to resist infections and hemorrhage. Oral infections increase the overall morbidity of cancer chemotherapy. If these infections are not discovered early and treated aggressively, they may be lethal following their systemic dissemination. Oral hemorrhaging may occur spontaneously and be profuse. Such incidents are terribly distressful to the patient, family and the professional care team. Fatal exsanguination has been reported.

Currently, antineoplastic drug therapy is being used with 40% of cancer patients either as a single treatment modality or as part of multi-modal therapy (chemotherapy, surgery, radiation). Some cancers respond well to single agent chemotherapy and others are treated with several agents in combination. New combinations and single agents are used in investigational clinical trials. The oral toxicity must be identified for all of these new agents and new combinations. Data show that nearly 50% of all individuals receiving chemotherapy will develop oral complication, most notably oral lesionary distinct in anatomical distribution and physical characteristics form other oral maladies resultant of fungal agents, bacteria and nutritional deficiencies. These complication include stomatitis, infection and hemorrhage Of this 50% incidence rate, 33% will develop one complication, 10% two complications and 3-4% will develop all three.

There is a plethora of scientific reports describing the multiple and varied oral complications as sequelae to cancer chemotherapy. Great detail has been used to describe these clinical entities. To a lesser degree, the scientific literature offers explanations for the pathogenesis of these oral lesions. Treatment protocols for these sequelae are more sparse and varied. Their development seems to be more empiric than scientific. An extensive literature search and a preliminary survey of some of the major cancer treatment centers in North America indicate that no treatment is presently available to prevent or significantly attenuate these oral complications. Clearly, there is a need for a proven, safe, comfortable and effective method and material to address this widespread and difficult problem.

SUMMARY OF THE INVENTION

The present invention involves a preparation adapted for prophylaxis and treatment of oral lesions. The claimed formulations include premixed forms of hydrogen peroxide and sodium bicarbonate as they exist in an aqueous formulation. Most surprisingly, premixed formulations provide a therapeutically effective treatment for the prophylaxis and treatment of oral lesions. A premixed formulation which includes hydrogen peroxide and which is therapeutically effective for non-bacterial oral lesions is most surprising, as hydrogen peroxide is known to be particularly unstable in solution.

Hydrogen peroxide is not described in any pharmaceutical agent. Typically, hydrogen peroxide solution has been used in the treatment of tissues of the oral cavity, where it is attacked by the enzyme catalase to provide the release of active oxygen. Hydrogen peroxide and sodium bicarbonate, together with table salt, have been used to destroy bacteria responsible for gum disease (Keyes procedure, substantially as described in S. Elder; "An Alternative to Gum Surgery" Modern Maturity, Aug.-Sep. 1980 pp. 31-32). However, the contact of these ingredients according to conventional practice, for example in the Keyes procedure, had to be prevented under "conventional protocols proposed in the art, until application to the oral cavity for therapeutic value. Device have even been patented to prevent the premixture of hydrogen peroxide and, for example, sodium bicarbonate (U.S. Pat. No. 4,687,663).

Surprisingly, the present inventors have discovered that a hydrogen peroxide and sodium bicarbonate premixed formulating has a profound therapeutic effect in healing oral lesions, particularly chemotherapeutic agent agent-induced oral lesions. Even more surprisingly, the inventor has found that the particularly described premixed aqueous solution of sodium bicarbonate and hydrogen peroxide may be used to effectively prevent the formation of oral lesions, including oral lesions in patients undergoing chemotherapy, by simple oral rinsing with the described SOL formulation.

The inventor has also found that, contrary to conventional teachings in the art, hydrogen peroxide in a premixed formulation with, for example, sodium bicarbonate, remains stable in the claimed concentration ranges over an extended period of time. Such eliminates the necessity for such separate "compartmentalized" devices as described by Schaeffer et al. (U.S. Pat. No. 4,687,663), as well as the messy and inconvenient "dipped toothbrush to hand" system with sodium bicarbonate and hydrogen peroxide described in the Keyes procedure (substantially as described e.g. in S. Elder:'-'An Alternative to Gum Surgery," Modern Maturity, August/September 1980, pp. 31-32).

The therapeutic preparation of the present invention comprises a premixed formulation of water, between about 0.1% and about 0.8% hydrogen peroxide and between about 0.1% and about 0.4% sodium bicarbonate. To produce such a preparation adapted for the prophylaxis and treatment of oral lesions, most particularly those induced by chemotherapeutic agents, most preferably involves dissolving hydrogen peroxide and sodium bicarbonate in an aqueous solution to produce a preparation having between about 0.1% and about 0.8% hydrogen peroxide and between about 0.1% and about 0.4% sodium bicarbonate. In more preferable embodiments of the present invention, the hydrogen peroxide is about 0.4% and the sodium bicarbonate is about 0.2%. Amazingly, these premixed formulations, with hydrogen peroxide, are found to be immensely valuable as both palliative agents and as a prophylactic regimen for a variety of non-bacterial oral pathologies, including stomatitis, gingivitis, candidiasis and, most particularly, those oral lesions incident chemotherapy.

Methods for prophylaxis and treatment of oral lesions are also included in the present invention. In one particular embodiment, the claimed method involves the step of initially providing a preparation preferably comprising water, between about 0.1% and about 0.8% hydrogen peroxide and between about 0.1% and 0.4% sodium bicarbonate. The hydrogen peroxide agent is thus presented in the formulation in a premixed form. Oral rinsing with said preparation, particularly multiple daily oral rinsing, is demonstrated to markedly enhance healing of oral lesions, as well as for impeding or preventing the development of oral lesions typically observed in patients being treated with a chemotherapeutic agent. Such chemotherapeutic agents are typically administered to patients as a treatment for cancer. Thus, the described methods and formulations may be most expeditiously employed for the treatment of oral lesions incident the use of chemotherapeutic agent.

In certain preferred embodiments, the preparation for prophylaxis and treatment of the present invention is defined further as comprising between about 20% and about 50% isotonic saline solution. In a preferred embodiment, the aqueous preparation of the present invention adapted for prophylaxis and treatment of oral lesions incident to cancer chemotherapy, comprise about 0.4% hydrogen peroxide, about 0.2% sodium bicarbonate and about 30% isotonic saline. In usage the preparation is used for oral rinsing on a daily multiple basis.

Upon mixture of the formulation ingredients, the formulation is most preferably to be stored in a light-impeding container so as to preserve the chemical nature of the mixture. The premixed formulation may be stored indefinitely without significant loss of therapeutic potency either at room temperature or refrigerated.

Most preferably, the light-impeding container may, for example, be of an amber color, although any hue or color of light impeding container may be employed.

DESCRIPTION OF THE PREFERRED EMBODIMENT

The present invention discloses a unique formulation, particularly an oral lavage, and methods found therapeutically effective for the prophylaxis and treatment of oral lesions comprising a premixed form of hydrogen peroxide and sodium bicarbonate in a formulation.

The formulation, otherwise referred to as SOL for purposes of the present invention, has been used to resolve, attenuate and prevent stomatitis in patients with solid and non-solid malignancies, all of which were treated with currently accepted chemotherapy protocols. Stomatitis is a reported significant side-effect in all of these treatment schedules. SOL not only performed well as a clinically effective agent for stomatitis but appeared to have a rather pronounced anti-plaque potential.

During the severe and prolonged myelosuppression following chemotherapy for leukemia, these patients should not and did not perform any dental flossing or tooth brushing. Oral physiotherapy abstinence is typically prescribed until the patients became hematologically stable so that flossing and tooth brushing would not produce any gingival hemorrhaging or life-threatening bacteremia/septicemia. Surprisingly, even without the attention of tooth brushing or flossing, the clinical crowns of the teeth, in these patients, remained clean and shiny during the severe neutropenic periods. None of the patients with natural dentition developed any significant gingival complications, such as gingivitis, Candida albicans, cheilitis, and aphthosis ulcer.

The presented examples involve patients subject to cancer chemotherapy as well as those suffering from stomatitis. Thus, the present oral lavage inventive treatment should have application for any individuals susceptible or subject to stomatitis-related oral lesions, as well as other pathologies of the oral cavity.

The following examples involving patients receiving chemotherapeutic agents are presented to describe preferred embodiments and utilities of the present invention and are not meant to limit the present invention unless otherwise stated in the claims appended hereto.

EXAMPLE I

Standard Oral Lavage

Standard oral lavage (SOL) is a therapeutic oral rinse of the present invention that has been developed for individuals with oral soft tissue problems. These individuals are most clearly exemplified as medical oncology patients subject to chemotherapy who are likely to be the greatest beneficiaries of SOL treatment. SOL had its genesis from an understanding of oral physiology and alternations of this physiology during and after chemotherapy treatments.

In the preferred embodiment therapeutically utilized herein the following SOL was used.

200 ml 3% hydrogen peroxide
400 ml normal saline
800 ml sterile water
3360 mg sodium bicarbonate
Peppermint concentrate (to provide

| -continued |
| --- |
| an acceptable flavor to the patient). |

The formula was packaged in a clear 1½ liter plastic jug, then inserted in an amber plastic bag for storage. The amber bag was to impede hydrogen peroxide from being deactivated by light. CEPACOL ® may also be included as a flavoring agent so as to enhance patient compliance. Where CEPACOL ® is desired as an ingredient, it may be added to the above formulation (about 100 ml CEPACOL ® per 1½ liters of complete SOL).

So formulated, the SOL may be stored indefinitely with essentially no loss of therapeutic efficiency. The formulation may be stored at room temperature or refrigerated with equal clinical efficacy upon patient use.

Pertinent to a description of the clinical efficacy of (SOL) the following examples are summaries of three patients who were being subjected to chemotherapy. These patients responded favorably to SOL and developed minimal or no stomatitis.

EXAMPLE II

M. J. was a 32 year old white female patient having a diagnosis of acute monocytic leukemia. She was treated with a standard remission-induction course of chemotherapy consisting of the following: Ara-C (170 mg per day) for seven days as a continuous intravenous infusion and Adriamycin (76 mg per day) for three days, intravenous push. She developed a severe stomatitis which required an intravenous morphine drip to manage pain.

There was severe ulceration of the labial and buccal mucous membranes which hemorrhaged sporadically and without provocation. The ventral surfaces of the tongue and the anterior floor of the mouth were similarly involved. Crenation of the tongue, due to fluid retention, produced additional traumatic ulcerations of its periphery from the base on the right side circumferentially to the left base. The uvula, soft palate, tonsillar pillars and the posterior oropharynx had multiple ulcerative lesions. Many of these oral lesions presented with pseudomembranes. Gingival hemorrhaging was bothersome at times. *Candida albicans* became a complicating component as an opportunistic infection.

SOL was minimally used as an oral rinse every two hours while the patient was awake and twice during the night. M. J. was instructed to rinse with two to three ounces of SOL as descried above and more frequently, if desired. A topical antifungal rinse was employed following meals and at bedtime to prevent and treat Candida. Candida is a fungal infection which is unrelated to the direct effects of the chemotherapeutic agents being administered to the patient.

Most surprisingly, through the use of SOL and careful clinical surveillance, the patient's initial severe stomatitis was resolved in six days during a period of pancytopenia. Since the remission-induction chemotherapy the patient received seven more courses of induction and consolidation chemotherapy. Several of these courses were high dose Ara-C and L-asparaginase. The only oral reaction noted was with the sequential high dose Ara-C courses of a one week duration. With this therapy, accompanied by SOL treatment, one oral ulcer developed with each week of treatment; the ulcer measuring about one millimeter in diameter. The patient was free from any other oral pathology.

EXAMPLE III

Another patient was W. W., a 49 year old white male with advanced colorectal cancer. This patient, with Duke's classification C adenocarcinoma of the rectum, was treated surgically with post-operative radiotherapy. Recurrence of this cancer was managed with high dose 5-fluorouracil administered as continuous intravenous infusion for five days. This regimen produced a moderately severe stomatitis that involved the labial and buccal mucosae and the latero-ventral surfaces of the tongue. It must be noted that this patient had multiple missing and curiously diseased teeth. Periodontally, these teeth showed significant bone loss.

Treatment of this 5-fluorouracil-induced stomatitis was performed with SOL in the same protocol described in Example II. Subsequent courses of 5-fluorouracil were administered to this patient using the identical dose and route of administration but accompanied with SOL therapy and no stomatitis was found to develop with steadily increasing CEA levels.

Patient W. W. was not totally compliant with the oral care and smoked rather heavily, typically two to three packs of cigarettes (Camels) per day. Tooth brushing and the use of dental floss were never part of the patient's health habits.

EXAMPLE IV

Another patient, J. L., was a 23 year old white male with a diagnosis of acute myeloblastic leukemia. This patient received a standard remission-induction chemotherapy regimen consisting of the following: Ara-C (190 mg per day) for seven days as a continuous intravenous infusion and Daunomycin (85 mg per day) for three days intravenous push.

As this chemotherapy quite consistently produces stomatitis, the patient was managed with the SOL protocol described in Example III. Only slight inflammation of the maxillary facial posterior gingivae on the left was noted. No oral ulcerations were seen. There were numerous consolidation treatments with m-AMSA/Ara-C and Ara-C/Daunomycin. Several of these regimen were high dose. No stomatitis developed in this patient during or after these treatments.

EXAMPLE V

The present example is provided to demonstrate the therapeutic action of the various combinations of hydrogen peroxide ($H_2O_2$), sodium chloride (NaCl), and sodium bicarbonate ($NaHCO_3$) as compared to the relative ineffective therapeutic value of solutions which include only one of these ingredients in the treatment and prevention of oral ulcers, particularly those oral lesions manifest in patients exposed to orally toxic chemotherapeutic agents.

The following solutions were employed in the study:

| Ingredient | Solution 1 | Solution 2 | Claimed Solution - Solution 3 |
| --- | --- | --- | --- |
| NaCl | <1% | <1% | <1% |
| $H_2O_2$ | 3% | — | 0.4% |
| $NaHCO_3$ | — | 0.2% | 0.2% |
| patient # oral lesions prevented | 0/18 = 0% | 0/29 = 0% | 16/16 = 100% |

The Solution #3 of hydrogen peroxide and sodium bicarbonate was prepared as a premixed solution and stored in an amber bottle until use.

Each patient from each of the respective groups rinsed with their respective oral lavage three times a day. All patients in each of the groups were receiving a chemotherapeutic agent associated with the development of stomatitis. The object of the oral lavage treatment was to achieve prevention of stomatitis in patients who had a prior history of having developed oral lesions after previous courses of treatment with chemotherapeutic agents. The oral lavage was also evaluated for its ability to decrease the duration of stomatitis and promote healing of the ulcerations.

The data collected from these studies indicates that solution of hydrogen peroxide alone (Solution 1—3% $H_2O_2$) or sodium bicarbonate alone (Solution 2—0.2% $NaHCO_3$) were ineffective for preventing the oral lesions incident chemotherapy treatment demonstrated by patients after prior chemotherapeutic treatments with no oral lavage. In contrast, patients demonstrating a prior history of chemotherapeutic-agent induced oral lesions after chemotherapeutic agent treatment who instead were treated with an oral lavage of a premixed formulation of hydrogen peroxide and sodium bicarbonate (3% $H_2O_2$+2% sodium bicarbonate) were effectively protected against the formation of oral lesions in all patients tested (16 out of 16 patients tested).

These data demonstrate that while a solution of hydrogen peroxide or sodium chloride alone are ineffective for preventing chemotherapeutic-agent induced oral lesionary, a premixed solution containing a mixture of both hydrogen peroxide and sodium bicarbonate, hydrogen peroxide thus being included in its chemically treated form, effectively prevented the development of oral lesionary previously observed in patients after having received chemotherapeutic agent in prior treatments. This result is surprising and most unexpected, as the mixture of hydrogen peroxide and sodium bicarbonate produces an immediate reaction, rendering the premixed solution, as per prior reports employing the Keyes procedure, therapeutically ineffective (See S. Elder (August–September 1980) Modern Maturity, pp. 31-32).

These results also demonstrate that the mixture of sodium bicarbonate with hydrogen peroxide does not reduce the effectiveness of the resulting premixed solution against preventing the particular and unique type of oral lesions incident the chemotherapy treatment of a patient.

EXAMPLE VI

Sol Prolonged Therapeutic Effectiveness

The present example is provided to demonstrate the prolonged stability and therapeutic effectiveness of the claimed formulation against oral lesions. The formulations were found to remain therapeutically effective up to 3 weeks after mixture in an aqueous solution. In addition, the presently described premixed formulation may be used to relieve xerostomia (dryness of the mouth), so as to increase oral hydration of the mouth as well as in the treatment of oral candidiasis, as well as for the debridement and cleaning of the oral soft tissues and mucus membranes. Use of the present formulations as an oral lavage manifests an elevation in the pH of the oral environment beyond the immediate time after oral rinsing, for at least ½ hour or more.

The formulation has also been observed to reduce the amount of plaque formation as well as retard the initial formation of plaque on tooth surfaces.

An oral lavage was formulated in a single batch of 1 liter according to the formula described in Example 1. The premixed hydrogen peroxide and sodium bicarbonate was then stored in a 1½ liter amber colored container at room temperature.

Patient V. F. (adult, female, 76 years of age) presented with a severe case of stomatitis, and was initiated on a four-times-daily oral treatment regimen with the described oral lavage. The patient was instructed not to eat or drink anything for 30 minutes after each treatment. The same batch of oral lavage was used over a three week treatment period, stored at room temperature near the patient's bedside.

V. F. developed stomatitis through a rather common set of circumstances seen in older adults. She suffered chronically from degenerative hip joint disease which produced continuous pain and dysfunctional ambulation. It became necessary to perform surgery where a prosthetic total hip joint was placed. Subsequent to this surgery, V. F. required significant doses of analgesic medications for pain during her rehabilitation process for the hip replacement prosthesis. Marked zerostomia (mouth dryness) was the major side effect of the analgesics which produced excessive oral mucosal friction, decreased oral pH and the resultant stomatitis. After 3 days of SOL (4× daily, as described), the stomatitis showed resolution and by day 5 was completely resolved. SOL therapy was continued for about 3 weeks as the dosage of analgesic medication was significantly reduced over this period of time. Stomatitis was resolved and subsequently resolved from reoccurring using the described SOL regimen.

Initial solution of SOL kept at her bedside first 2 weeks in an amber bag. Subsequent formulations of the SOL were prepared. Patient V. F. used approximately 120 ml day of the SOL. Thus, a 1 liter batch is about a 2-week supply.

Stomatitis results in dryness of the mouth and logarithmic loss of salivary buffering capacity (i.e., pH 7 to 6 for example is a 10-fold reduction). An extreme decrease in pH therefore results with this condition, wherein the oral cavity becomes extremely acidic.

The patient's oral stomatitis condition was observed to improve steadily with each treatment. The stomatitis was virtually eliminated upon the 3rd week of treatment.

The results observed demonstrate that the disclosed formulation, with its premixed forms of hydrogen peroxide and sodium bicarbonate, provide a pharmacologically active preparation effective for the treatment of oral pathologies.

Changes may be made in the elements and components described herein or in the steps or the sequence of steps of the method described herein without departing from the concept and scope of the invention as defined in the following claims.

What is claimed is:

1. A premixed hydrogen peroxide and sodium bicarbonate pharmaceutical formulation for the treatment of oral lesions consisting essentially of between about 0.1% and about 0.8% hydrogen peroxide and between about 0.1% and about 0.4% sodium bicarbonate, together in sterile saline or sterile water.

2. An oral lavage preparation for prophylaxis and treatment of oral lesions, the preparation consisting essentially of a premixed formulation of water, about 0.4% hydrogen peroxide, about 0.2% sodium bicarbonate and about 30% isotonic saline.

3. The oral lavage of claim 2 wherein the oral lesions are incident therapy of a patient with a chemotherapeutic agent.

4. The oral lavage of claim 2 wherein the oral lesions are stomatitis lesions.

5. The oral lavage of claim 2 wherein the oral lavage is stored in a light impeding container.

6. The pharmaceutical formulation of claim 1 wherein the hydrogen peroxide is in premixed aqueous form in contact with sodium bicarbonate.

7. A method for prophylaxis and treatment of oral lesions in a patient, the method comprising the steps of:
identifying a susceptibility to a presence of oral lesions in a patient;
preparing a premixed formulation consisting essentially of about between about 0.1% and about 0.8% hydrogen peroxide, about between about 0.1% and about 0.4% sodium bicarbonate and about 30% isotonic saline;
storing said premixed formulation in a light-impeding container; and
orally rinsing the identified patient multiple times per day for a period of time at least as long as the lesion is present with the premixed formulation.

8. The method of claim 7 wherein the oral lesions are induced by a chemotherapeutic agent.

9. A method for producing an oral lavage for use in the prevention of chemotherapeutic agent-induced oral lesions comprising:
preparing a premixed aqueous solution consisting essentially of about 0.4% hydrogen peroxide, about 0.2% sodium bicarbonate and about 30% isotonic saline; and
storing the premixed aqueous solution in a light impeding container.

10. A method for producing an oral lavage for use in the prophylaxis and treatment of chemotherapeutic agent-induced oral lesions, the method comprising:
dissolving hydrogen peroxide and sodium bicarbonate in an aqueous solution to produce a preparation consisting of between about 0.1% and about 0.8% hydrogen peroxide and between about 0.1% and about 0.4% sodium bicarbonate; and
storing the preparation in a light impeding container until use.

11. A method for treatment of chemotherapeutic agent-induced oral lesions, the method comprising:
identifying a patient having chemotherapeutic agent-induced oral lesions;
orally treating the patient with a premixed oral lavage consisting essentially of water, between about 0.1% and about 0.8% hydrogen peroxide and between about 0.1% and about 0.4% sodium bicarbonate; and
repeating the treatment of the patient until the chemotherapy-induced lesions are reduced in size.

12. An oral lavage for prophylaxis of chemotherapeutic agent-induced oral lesions, the oral lavage consisting essentially of water, between about 0.1% and about 0.8% hydrogen peroxide and between about 0.1% and about 0.4% sodium bicarbonate.

13. The oral lavage of claim 12 defined further as comprising between about 20% and about 50% isotonic saline solution.

14. The oral lavage of claim 12 defined further as comprising about 0.4% hydrogen peroxide.

15. The oral lavage of claim 12 defined further a comprising ethyl alcohol.

16. The oral lavage of claim 12 defined further as comprising about 0.2% sodium bicarbonate.

17. The method of claim 7 or claim 11 wherein the oral lavage is defined further as including about 0.4% hydrogen peroxide, about 0.2% sodium bicarbonate and about 30% isotonic saline.

18. The method of claim 7 or claim 11 wherein the oral lavage is defined further as comprising between about 20% and about 50% isotonic saline solution.

19. The method of claim 7 or claim 11 wherein the oral lavage is defined further as comprising about 0.4% hydrogen peroxide.

20. The method of claim 9 or claim 10 wherein the oral lavage is defined further as comprising about 0.2% sodium bicarbonate.

21. The method of claim 9 or claim 10 wherein the chemotherapeutic agent-induced oral lesion is induced by the chemotherapeutic agent methotrexate, 5-fluorouracil, Ara-C, cis-platinum, m-AMSA, daunorubicin, bleomycin, cytosine arabinoside or a mixture thereof.

* * * * *